(12) United States Patent
Aarts et al.

(10) Patent No.: US 8,876,576 B2
(45) Date of Patent: Nov. 4, 2014

(54) METHOD FOR SHARPENING MICROPROBE TIPS

(75) Inventors: Arno Aarts, Leuven (BE); Robert Puers, Blanden (BE)

(73) Assignees: IMEC, Leuven (BE); Katholieke Universiteit Leuven, K.U. Leuven R&D, Leuven (BE)

( * ) Notice: Subject to any disclaimer, the term of this patent is extended or adjusted under 35 U.S.C. 154(b) by 167 days.

(21) Appl. No.: 13/473,877

(22) Filed: May 17, 2012

(65) Prior Publication Data

US 2012/0295520 A1    Nov. 22, 2012

(30) Foreign Application Priority Data

May 20, 2011  (EP) .................................. 11166865

(51) Int. Cl.
| | | |
|---|---|---|
| *B24B 19/16* | (2006.01) | |
| *A61B 5/04* | (2006.01) | |
| *A61B 5/00* | (2006.01) | |

(52) U.S. Cl.
CPC ............. *A61B 5/04001* (2013.01); *A61B 5/685* (2013.01); *B24B 19/16* (2013.01); *A61B 2562/125* (2013.01)
USPC .............................. 451/49; 451/382; 451/389

(58) Field of Classification Search
CPC ....... B24B 19/16; B24B 19/165; B24D 15/06
USPC ............ 451/28, 41, 45, 49, 63, 367, 382, 389
See application file for complete search history.

(56) References Cited

U.S. PATENT DOCUMENTS

| | | | | |
|---|---|---|---|---|
| 165,540 | A | * | 7/1875 | Cashin .......................... 451/320 |
| 2,205,964 | A | * | 6/1940 | Taylor ........................... 451/370 |
| 2,389,069 | A | * | 11/1945 | Mascarenhas ................ 451/370 |
| 2,443,937 | A | * | 6/1948 | Torteson ....................... 451/370 |
| 2,740,240 | A | * | 4/1956 | Rugels .......................... 451/370 |
| 3,910,677 | A | | 10/1975 | Becker et al. |
| 4,430,358 | A | * | 2/1984 | Wada ........................... 427/2.28 |
| 5,155,943 | A | * | 10/1992 | Matsutani et al. ............... 451/28 |
| 5,199,225 | A | * | 4/1993 | Esposito ....................... 451/555 |
| 5,270,543 | A | * | 12/1993 | Visser et al. .................... 850/56 |
| 5,944,592 | A | * | 8/1999 | Hall et al. ...................... 451/321 |
| 6,024,629 | A | * | 2/2000 | Takekoshi ....................... 451/28 |
| 7,412,767 | B2 | * | 8/2008 | Kim et al. ....................... 29/879 |
| 7,462,800 | B2 | * | 12/2008 | Tunaboylu et al. ...... 219/121.69 |
| 7,959,494 | B1 | * | 6/2011 | Pietrzak .......................... 451/45 |

(Continued)

FOREIGN PATENT DOCUMENTS

| | | |
|---|---|---|
| DE | 4107871 A1 | 9/1992 |
| EP | 0619983 A2 | 10/1994 |

(Continued)

*Primary Examiner* — George Nguyen
(74) *Attorney, Agent, or Firm* — McDonnell Boehnen Hulbert & Berghoff LLP (57) ABSTRACT

The present disclosure is related to a method for sharpening the tip of a microprobe, in particular a neural probe or an array of neuroprobes having a common base portion. The probes have a constant thickness and a chisel-shaped tip portion. The probes are attached to the slanted side of a wedge-shaped carrier, with the probe tips placed in close proximity to the edge of the carrier, for example extending over said edge. The base of the carrier is then subjected to a grinding step, possibly followed by a polishing step, so that the probe tips of the probes are ground to form a sharp pointed tip shape.

13 Claims, 5 Drawing Sheets

(56) References Cited

U.S. PATENT DOCUMENTS

| | | | |
|---|---|---|---|
| 2003/0064662 A1* | 4/2003 | Minami | 451/5 |
| 2003/0090280 A1* | 5/2003 | Maekawa et al. | 324/754 |
| 2005/0253606 A1* | 11/2005 | Kim et al. | 324/754 |
| 2007/0178814 A1* | 8/2007 | Sato et al. | 451/49 |
| 2008/0106292 A1* | 5/2008 | Chui et al. | 324/758 |
| 2008/0108221 A1* | 5/2008 | Kim et al. | 438/652 |
| 2008/0220556 A1* | 9/2008 | Ko et al. | 438/52 |
| 2010/0155253 A1* | 6/2010 | Kim et al. | 205/122 |
| 2011/0217665 A1* | 9/2011 | Walsh et al. | 433/29 |
| 2012/0083680 A1* | 4/2012 | Carr | 600/373 |
| 2012/0196513 A1* | 8/2012 | Bagley et al. | 451/45 |
| 2013/0029564 A1* | 1/2013 | Yoshimura | 451/49 |
| 2013/0072808 A1* | 3/2013 | Neves et al. | 600/544 |

FOREIGN PATENT DOCUMENTS

| | | |
|---|---|---|
| EP | 1884192 A1 | 2/2008 |
| JP | 2002341173 | 11/2002 |
| JP | 2003315563 | 11/2003 |
| WO | WO2010/005479 A1 | 1/2010 |

\* cited by examiner

METHOD FOR SHARPENING MICROPROBE TIPS

CROSS-REFERENCE TO RELATED APPLICATIONS

This application claims priority under 35 U.S.C. §119(b) to European Patent Application EP 11166865.3, filed on May 20, 2011, the contents of which are fully incorporated herein by reference.

FIELD

The present disclosure is related to microprobe devices, in particular to single shaft or arrays of neural probes containing embedded micro-electronic structures, such as CMOS structures.

BACKGROUND

Figure 1:
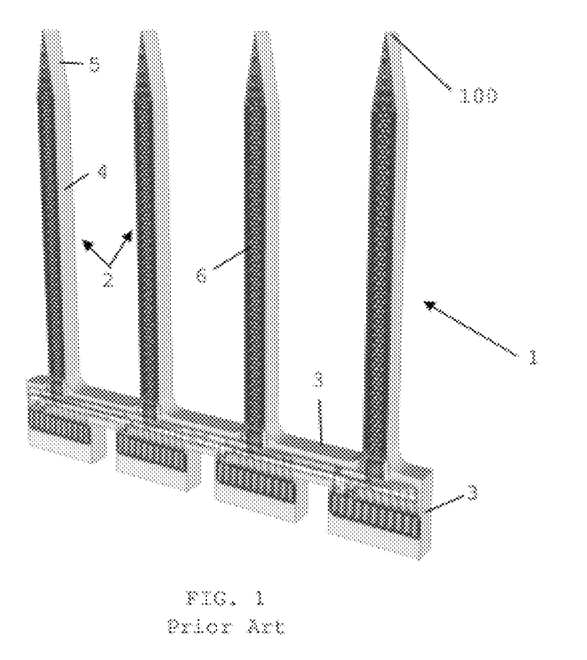
FIG. 1 illustrates a neural probe array according to the prior art.

FIG. 1 shows a probe array 1 as known in the art. The array comprises a number of probes 2, connected by a base portion 3. Each probe comprises an elongate shaft portion 4 and a triangular chisel shaped tip portion 5, with micro-electronic structures 6 embedded in the shaft portions. The probes 2 of the array 1 have an essentially constant thickness, said thickness being the same for the shaft portions 4 and the tip portions 5. Said thickness corresponds to the thickness of the semiconductor substrate from which the probes are produced. The probe tips are thus formed by a straight edge 100 with a length that equally corresponds to said substrate thickness. This tip shape is not able to pierce through the brain membrane, also known as the Dura matter, without causing a harmful dimpling of the Dura.

Using thinner substrates or etching the probe tips to reduce the thickness leads to probes with insufficient mechanical properties to perform the required functions. Other techniques are known, such as anisotropic etching techniques which etch certain Si-planes faster than others. However, this is still a technically complex and time-consuming approach.

Overview

The disclosure is related to a method and probe arrays as described in the appended claims. The disclosure is thus related to a method for sharpening the tip of a microprobe, comprising, for example, the steps of:
- providing at least one probe said probe having a base portion, an elongate shaft portion and a triangular chisel-shaped tip portion, at least said shaft and tip portions having an essentially constant thickness extending between a first and second surface of the probe,
- providing a carrier having a first and second flat outer surface oriented at an angle to each other, so that said surfaces are joined by an edge of said carrier,
- attaching the first surface of the probe to the second surface of the carrier, with the base portion and the majority of the shaft portion attached to said second surface and the tip portion being in close proximity to said edge,
- subjecting the first surface of the carrier and at least part of the tip portion of the probe to a grinding step, to thereby remove material at least from said triangular, chisel shaped tip portion of the probe.

According to an embodiment of the method, an array of said probes is provided, said array comprising a common base portion, and parallel probes extending outward from said base portion, at least the elongate shaft portions and chisel shaped tip portions of said probes having an essentially constant thickness extending between a first and second surface of the probe array, and the first surface of said array is attached to said second surface of the carrier, with the base portion and the majority of each shaft portion attached to the second surface, and the triangular chisel shaped tip portions being in close proximity to the edge, and wherein material is removed from the triangular tip portions of all of said probes.

According to an embodiment, at least part of said triangular, chisel shaped tip portion(s) is (are) extending outward from said edge, so that said part of the triangular tip portion(s) extend(s) below the first surface of the carrier when said first surface is held horizontally, and wherein substantially no material of the carrier is removed during said grinding step.

According to another embodiment, the probe(s) do(es) not extend outward from the edge, and wherein the carrier material and the probe tip material are removed simultaneously during said grinding step.

Said edge may be shaped as a straight line. Said probe(s) may be placed perpendicularly to said edge.

The location on the carrier block onto which the probe(s) is (are) attached may be provided with an alignment structure. Said alignment structure may comprise one or more grooves into which said probe or probes may be placed. Said alignment structure may be a negative imprint of the probe or probe array.

According to an embodiment, the grinding step is done by placing the carrier on a rotating grinding disc and applying pressure on the carrier. The grinding step may be followed by a polishing step.

According to an embodiment, the grinding step is continued so as to obtain a sharp pointed tip, lying in the plane defined by the second surface of the probe or probe array.

According to another embodiment, the grinding step is followed by the steps of:
- attaching the second surface of the probe or probe array to the second surface of the carrier, with the base portion and the majority of the shaft portion of each probe attached to said second surface and the tip portion being in close proximity to said edge,
- subjecting the first surface of the carrier and at least part of the tip portion of the probe(s) to a grinding step, to thereby remove material at least from said triangular, chisel shaped tip portion(s) of the probe(s), so as to obtain a sharp pointed tip lying in between the planes defined by the first and second surface of the probe or probe array.

According to an embodiment, the grinding step is done with a grinding surface having an average grain size between 5 μm and 20 μm.

These as well as other aspects, advantages, and alternatives, will become apparent to those of ordinary skill in the art by reading the following detailed description, with reference where appropriate to the accompanying drawings.

BRIEF DESCRIPTION OF THE FIGURES

Various exemplary embodiments are described herein with reference to the following drawings, wherein like numerals denote like entities. The drawings described are schematic and are non-limiting.

DETAILED DESCRIPTION

Figure 2:
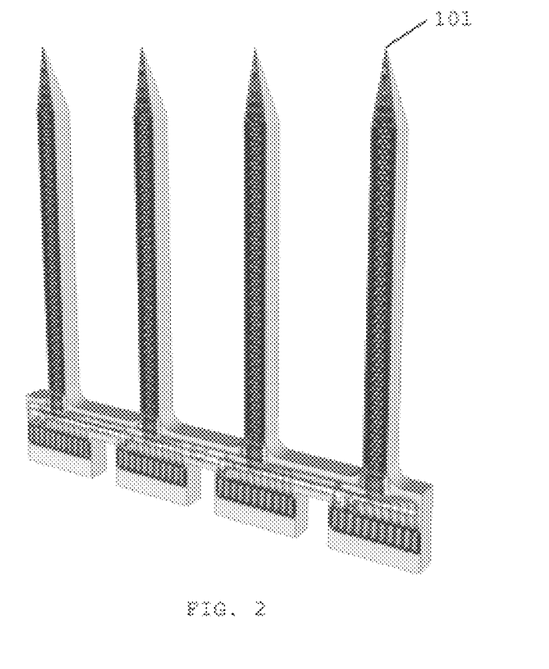
FIG. 2 illustrates an example probe array obtainable by the method of the disclosure.

FIG. 2 shows an example neural probe array obtainable by the method of the disclosure. Each probe has a sharp pointed tip 101, able to pierce through the Dura without the dimpling effect.

Figure 3:
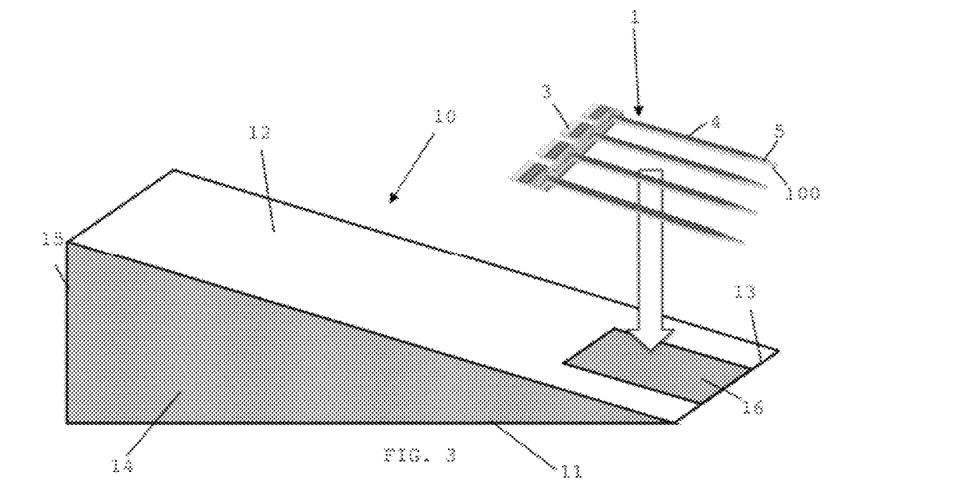
FIG. 3 shows an example carrier block usable in the method of the disclosure, and an example attachment location of a probe array to said carrier block.

Example embodiments of the method of producing such a probe array are illustrated in FIGS. 3-7. The method as described hereafter is also applicable to a single shaft probe. Referring first to FIG. 3, a probe array 1 is provided, which is an array as shown in FIG. 1, i.e. having an essentially constant thickness of the elongate shaft portions 4 and the triangular chisel-shaped tip portions 5, i.e. the probe array has a first and second flat surface 7/8 (see FIG. 3), the thickness of the probes extending between said surfaces. The probe array is temporarily attached by its first surface 7 to a carrier 10, which is for example a solid carrier block, e.g. made of aluminium. The carrier block shown in FIG. 3 is wedge-shaped, with a flat base surface 11 and a slanted top surface 12, forming a sharp angle with respect to the base surface, so that a straight edge 13 is formed between the base and top surfaces 11 and 12. The carrier 10 further comprises parallel side walls 14 and a back wall 15 perpendicular to the base surface. Other outer shapes of the carrier are possible, as long as the carrier comprises a first and second surface 11/12 forming a wedge, i.e. being oriented at a sharp angle with respect to each other, and joined by an edge 13 of the carrier.

Figure 4:
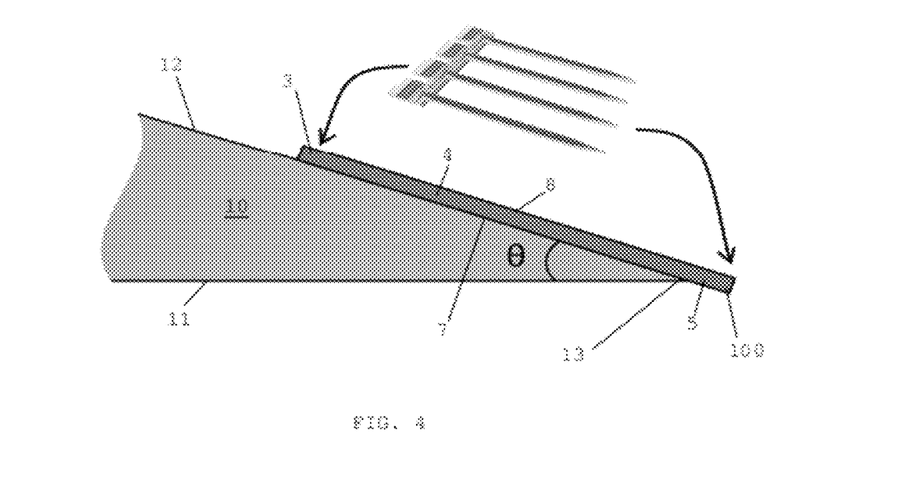
FIG. 4 shows an example probe array attached to an example carrier block.

As seen in FIGS. 3 and 4, the probe array 1 is releasably attached to a contact location 16 of the carrier's slanted top surface 12, with at least part of the triangular tip portions 5 extending over the edge 13, all triangular tip portions being placed at the same distance from the edge 13. This means that a portion of the probes extends downward from the base surface 11 when said base surface is placed horizontally (see FIG. 4). In the case shown in FIG. 4, the base 3 and shafts 4 of the probe array 1 are removably attached to the top surface 12 of the carrier block 10 with a suitable temporary adhesive, e.g. a resin or a wax. The contact location 16 on the slanted surface 12 of the block may be provided with an alignment structure, for example comprising a set of grooves oriented perpendicularly to the edge 13, and at a mutual distance corresponding to the mutual distance of the probes in the array, so that the probes fit into said grooves. The alignment structure may be a negative imprint of the entire probe array, including the base portion 3, so that the entire array 1 can be fitted into the carrier block's top surface 12. The above named adhesive may be used in addition to the alignment structure. Extending outward from the carrier edge 13 is the straight edge 100 of the chisel-shaped triangular probe tips 5. The straight edge 100 is essentially perpendicular to the surface 12 of the carrier.

Figure 5:
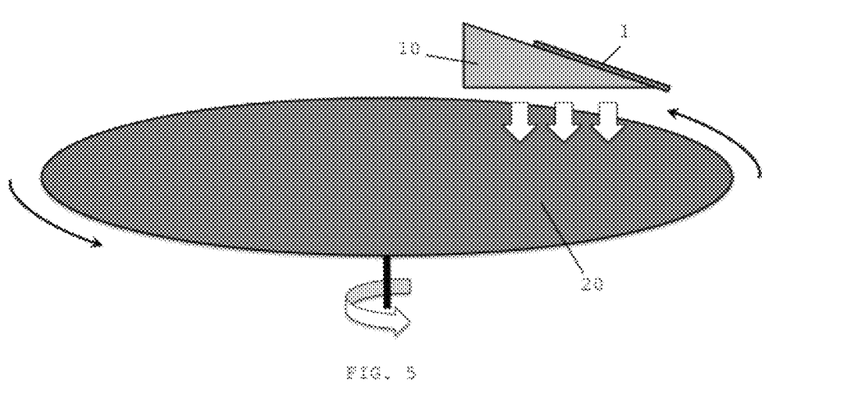
FIG. 5 shows an example rotating grinding tool being used in conjunction with the carrier block and a probe array attached thereto.
Figure 6:
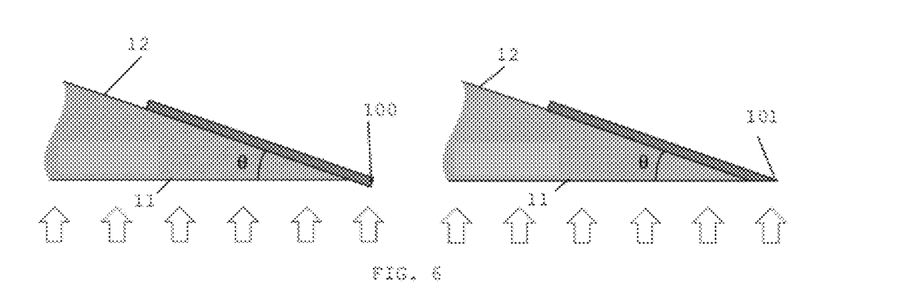
FIG. 6 shows the shape of the probe tips before and after grinding, according to one embodiment of the method of the disclosure.

Then the carrier block/probe array combination may be subjected to a grinding step as illustrated in FIG. 5. A known grinding/polishing tool may be used, having a rotating grinding disc 20 onto which the carrier block 10 can be placed with a suitable pressure. The carrier block can be fixed onto a micro-drive which lowers the carrier onto the rotating grinding/polishing disk. Suitable grinding/polishing tools that can be used are, for example, the Saphir 320/330 series from ATM. In the case shown in FIG. 4, the carrier material, the material of the grinding surface, the applied pressure and grinding time are chosen so that substantially no or very little material is removed from the carrier block's base surface 11 during said grinding step, while all the material of the probe tips extending below the base surface 11 is removed during said step. The result of the grinding step is shown in FIG. 6. After a suitable grinding time, the portion of the probes extending below the base surface 11 is removed, and a sharp tip 101 is formed at the outer end of the probes. The angle θ of the carrier block 10 is thereby substantially transferred to the probe tips.

Figure 7:
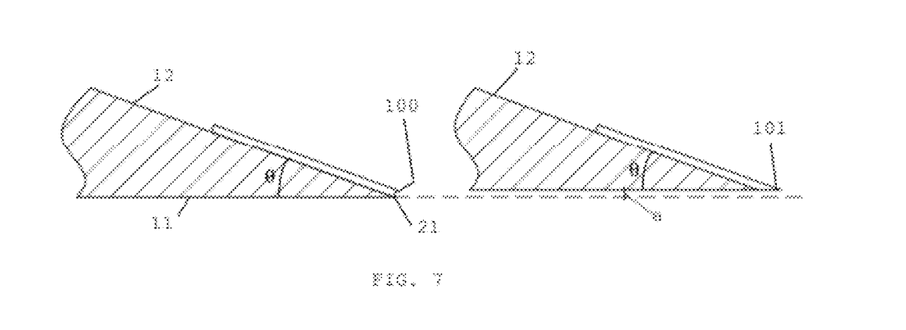
FIG. 7 shows the shape of the probe tips before and after grinding, according to another embodiment of the method of the disclosure.

Another example embodiment is illustrated in FIG. 7. In this case, the material of the carrier 10, the material of the grinding surface, the grinding pressure and time are chosen so that the carrier block's base surface 11 is thinned during the grinding step, together with the probe tip. The probes are attached to the carrier block without the triangular tip portions 5 extending over the edge 13, for example with the lower end 21 of the tip placed on the edge 13, as shown in FIG. 7. During the grinding step, a thickness 'a' of the carrier block and of the tip material is simultaneously removed, leading also to a sharp tip 101 at the end of the grinding step, with the angle θ of the carrier block transferred to the probe tip. In both embodiments shown in FIGS. 6 and 7, the tip 101 lies in the plane defined by the probe array's second surface 8.

Variants of the above-described embodiments are included in the scope of the appended claims. The edge 13 may be curved instead of straight. This allows the formation of probe tips of different shape and size in one grinding step. Likewise, instead of placing the probes of an array at the same distance to a straight edge 13, it is possible to place the array at an angle to the edge. Instead of an array of probes, a single probe may be sharpened by the method of the disclosure. The angle θ is a sharp angle, i.e. lower than 90°, and for example lower than 45°.

The carrier 10 may be but is not necessarily a solid block. The grinding step can be followed by a polishing step, which may release the stresses induced by the grinding process. The polishing step can be performed in the same tool as the grinding step, e.g. by applying another polishing disk onto the rotating table of a rotatable grinding tool.

Instead of grinding only from the backside of the probe or probe array, resulting in a pointed tip in the second surface 8 of the probe or probe array, it is also possible to grind from both sides resulting in a pointed tip located in between the first and second surface 7/8, and may be at the centre of the shaft's thickness. This can be done by grinding the probe in two steps: in the first step, the probe is attached by its first flat side 7 to the carrier block 10 as described above and a portion of the tip is removed by grinding and possibly polishing, for example until at least about half of the straight edge 100 is removed. Then the probe is removed, reversed and re-attached by its second side 8, and a second grinding and possibly polishing step is done until a sharp tip is obtained, said tip lying in between the first and second surface 7/8 of the probe. Both steps can be done by the method of the disclosure according to the embodiment of FIG. 6 or 7.

The sharpness of the carrier's edge 13 may not be a crucial parameter. For example, it is possible to grind the tip of the probe while the carrier contains a blunt edge 13. Since the angle of the carrier 10 and the thickness of the tip are known one can calculate how far the chisel shaped tip 5 should extend from the edge 13.

It is pointed out that the method of the disclosure must be viewed with regard to methods in the same technical domain, i.e. the domain of microprobes. More specifically, this concerns probes that may have a thickness between about 30 μm and 100 μm and lengths ranging from 1 mm to a few centimeters, with micro-electronic structures mounted on one side of the probe. Even though the principle of sharpening a knife edge with the help of a wedge-shaped tool may be known, as for example illustrated by document U.S. Pat. No. 5,199,225, the effectiveness of such a method could not have been predicted in the field of microprobes. For instance, the fact that it is possible to sharpen probes of such microscopic dimensions without damaging the probes and/or the micro-electronic components could not have been expected. The following example proves the feasibility of the disclosed method, illustrating also that the coarseness of the grinding paper must be chosen carefully in order to avoid damage to the probes.

EXAMPLE

Figure 8:
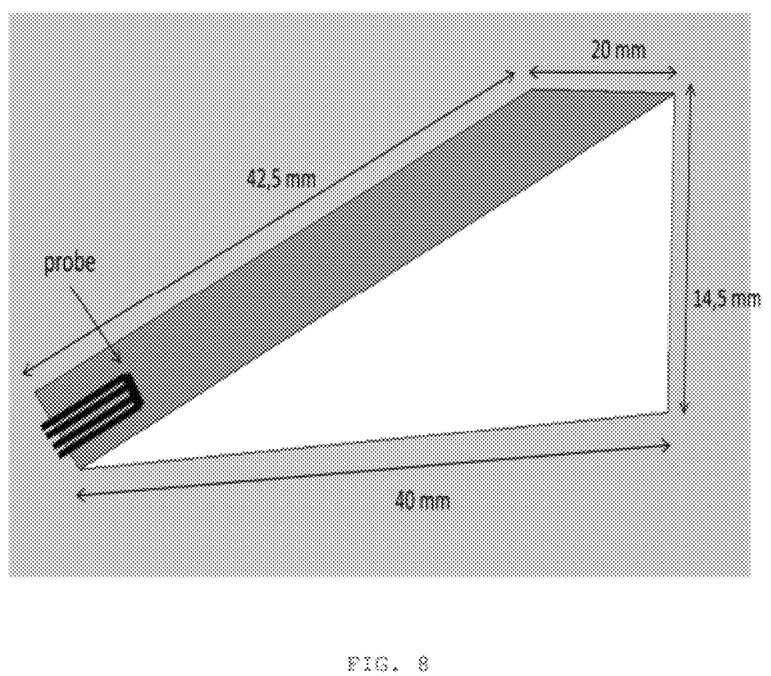
FIG. 8 shows an example of the dimensions of a carrier block usable in the method of the disclosure.

A test was performed with the following materials and steps:
- probe array: four shaft silicon probe array with length and thickness of about 8 mm and 100 micrometer,
- carrier: Aluminium block with dimensions as shown in FIG. 8,
- the attachment of the probe array to the carrier was done using tissue adhesive which dissolves in acetone. Alignment of the probe was performed under an optical microscope,
- the grinding step was done during 5 minutes. This parameter may vary strongly with pressure and spinning speed of the grinding disk and particle size of the grinding disk. Within this particular experiment the carrier was manually held in place during grinding. A Saphir330 grinding machine was used; as wet grinding paper a P4000 (FEPA-norm: average grain size 6.5 μm) was used at a spinning speed of 150 rpm. Optical microscopic inspection has been done after each minute of grinding. During this experiment no polishing step has been performed.
- the result was a sharp tip as shown in FIG. 4.

The same experiment was done with grinding paper having a more coarse surface, in particular P2500 (average grain size 10 μm), P1200 (av. grain size 15 μm), P400 (av. grain size 35 μm) and P220 (av. grain size 60 μm). The tests with P2500 and P1200 yielded good probe tips, but the coarsest grinding papers (P400 and P220) clearly induced damage on the probe tip and/or the micro-electronic structures on the backside of the tip. Therefore, according to an example embodiment, the grinding step is performed with grinding paper having an average grain size between 5 μm and 20 μm.

Figure 9:
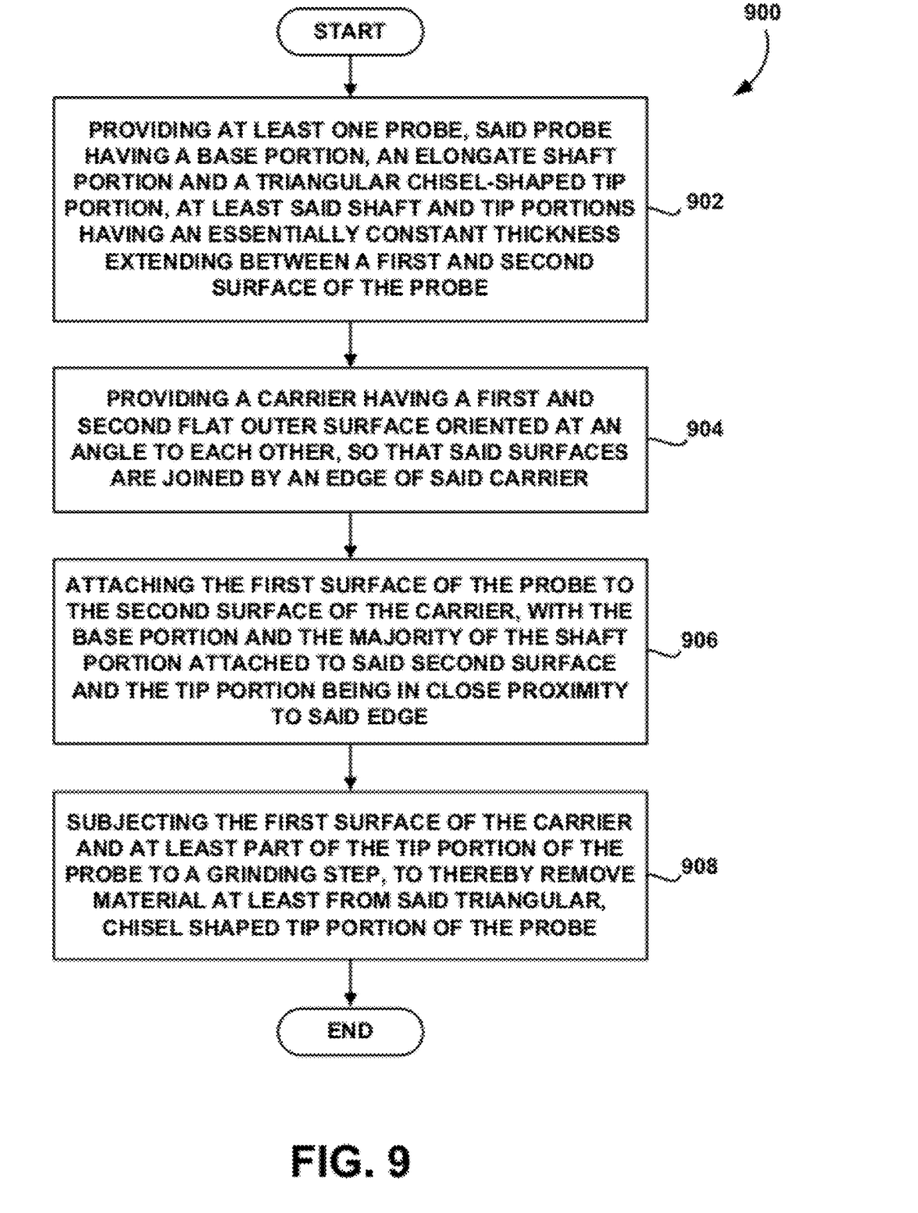
FIG. 9 illustrates a method in accordance with an example of the present disclosure.

An example method 900 in accordance with the present disclosure is depicted in FIG. 9. The method 900 includes, at step 902, providing at least one probe, said probe having a base portion, an elongate shaft portion and a triangular chisel-shaped tip portion, at least said shaft and tip portions having an essentially constant thickness extending between a first and second surface of the probe. Further, the method 900 includes, at step 904, providing a carrier having a first and second flat outer surface oriented at an angle to each other, so that said surfaces are joined by an edge of said carrier. Still further, the method 900 includes, at step 906, attaching the first surface of the probe to the second surface of the carrier, with the base portion and the majority of the shaft portion attached to said second surface and the tip portion being in close proximity to said edge. Yet still further, the method 900 includes, at step 908, subjecting the first surface of the carrier and at least part of the tip portion of the probe to a grinding step, to thereby remove material at least from said triangular, chisel shaped tip portion of the probe.

While the invention has been illustrated and described in detail in the drawings and foregoing description, such illustration and description are to be considered illustrative or exemplary and not restrictive. Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The foregoing description details certain embodiments of the invention. It will be appreciated, however, that no matter how detailed the foregoing appears in text, the invention may be practiced in many ways, and is therefore not limited to the embodiments disclosed. It should be noted that the use of particular terminology when describing certain features or aspects of the invention should not be taken to imply that the terminology is being re-defined herein to be restricted to include any specific characteristics of the features or aspects of the invention with which that terminology is associated.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

The invention claimed is:

1. A method for sharpening the tip of a microprobe, the method comprising the steps of:
   providing at least one probe, each probe of said at least one probe having a base portion, an elongate shaft portion and a triangular chisel-shaped tip portion, at least said shaft and tip portions having an essentially constant thickness extending between a first and second surface of the probe;
   providing a carrier having a first and second flat outer surface oriented at an angle to each other, so that said surfaces are joined by an edge of said carrier; and
   for each probe of said at least one probe,
   (i) attaching the first surface of the probe to the second surface of the carrier, with the base portion and the majority of the shaft portion attached to said second surface and the tip portion being in close proximity to said edge; and
   (ii) subjecting the first surface of the carrier and at least part of the tip portion of the probe to a grinding step, to thereby remove material at least from said triangular, chisel shaped tip portion of the probe,
   wherein at least part of said triangular, chisel shaped tip portion is extending outward from said edge, so that said part of the triangular tip portion extends below the first surface of the carrier when said first surface is held horizontally, and wherein substantially no material of the carrier is removed during said grinding step.

2. The method of claim 1, wherein an array of said probes is provided, said array comprising a common base portion, and parallel probes extending outward from said base portion, at least the elongate shaft portions and chisel shaped tip portions of said probes having an essentially constant thickness extending between a first and second surface of the probe array, and wherein the first surface of said array is attached to said second surface of the carrier, with the base portion and the majority of each shaft portion attached to the second surface, and the triangular chisel shaped tip portions being in close proximity to the edge, and wherein material is removed from the triangular tip portions of all of said probes.

3. The method of claim 1, wherein said edge is shaped as a straight line.

4. The method of claim 1, wherein each probe of said at least one probe is placed perpendicularly to said edge.

5. The method of claim 1, wherein said grinding step is followed by a polishing step.

6. The method of claim 1, wherein said grinding step is continued so as to obtain a sharp pointed tip, lying in the plane defined by the second surface of the probe.

7. The method of claim 1, wherein said grinding step is followed by the steps of:
for each probe of said at least one probe,
(i) attaching the second surface of the probe to the second surface of the carrier, with the base portion and the majority of the shaft portion of the probe attached to said second surface and the tip portion being in close proximity to said edge; and
(ii) subjecting the first surface of the carrier and at least part of the tip portion of the probe to a grinding step, to thereby remove material at least from said triangular, chisel shaped tip portion of the probe, so as to obtain a sharp pointed tip lying in between the planes defined by the first and second surface of the probe.

8. The method according to claim 1, wherein said grinding step is done with a grinding surface having an average grain size between 5 µm and 20 µm.

9. A method for sharpening the tip of a microprobe, the method comprising the steps of:
providing at least one probe, each probe of said at least one probe having a base portion, an elongate shaft portion and a triangular chisel-shaped tip portion, at least said shaft and tip portions having an essentially constant thickness extending between a first and second surface of the probe;
providing a carrier having a first and second flat outer surface oriented at an angle to each other, so that said surfaces are joined by an edge of said carrier; and
for each probe of said at least one probe,
(i) attaching the first surface of the probe to the second surface of the carrier, with the base portion and the majority of the shaft portion attached to said second surface and the tip portion being in close proximity to said edge; and
(ii) subjecting the first surface of the carrier and at least part of the tip portion of the probe to a grinding step, to thereby remove material at least from said triangular, chisel shaped tip portion of the probe, wherein the probe does not extend outward from the edge such that a lower end of the tip portion does not extend from the edge, and wherein the carrier material and the probe tip material are removed simultaneously during said grinding step.

10. A method for sharpening the tip of a microprobe, the method comprising the steps of:
providing at least one probe, each probe of said at least one probe having a base portion, an elongate shaft portion and a triangular chisel-shaped tip portion, at least said shaft and tip portions having an essentially constant thickness extending between a first and second surface of the probe;
providing a carrier having a first and second flat outer surface oriented at an angle to each other, so that said surfaces are joined by an edge of said carrier; and
for each probe of said at least one probe,
(i) attaching the first surface of the probe to the second surface of the carrier, with the base portion and the majority of the shaft portion attached to said second surface and the tip portion being in close proximity to said edge; and
(ii) subjecting the first surface of the carrier and at least part of the tip portion of the probe to a grinding step, to thereby remove material at least from said triangular, chisel shaped tip portion of the probe;
wherein a location on the carrier block onto which each probe of the at least one probe is attached is provided with an alignment structure.

11. The method of claim 10, wherein said alignment structure comprises one or more grooves into which said at least one probe may be placed.

12. The method of claim 10, wherein said alignment structure is a negative imprint of the at least one probe.

13. A method for sharpening the tip of a microprobe, the method comprising the steps of:
providing at least one probe, each probe of said at least one probe having a base portion, an elongate shaft portion and a triangular chisel-shaped tip portion, at least said shaft and tip portions having an essentially constant thickness extending between a first and second surface of the probe;
providing a carrier having a first and second flat outer surface oriented at an angle to each other, so that said surfaces are joined by an edge of said carrier; and
for each probe of said at least one probe,
(i) attaching the first surface of the probe to the second surface of the carrier, with the base portion and the majority of the shaft portion attached to said second surface and the tip portion being in close proximity to said edge; and
(ii) subjecting the first surface of the carrier and at least part of the tip portion of the probe to a grinding step, to thereby remove material at least from said triangular, chisel shaped tip portion of the probe;
wherein the grinding step is done by placing the carrier on a rotating grinding disc and applying pressure on the carrier.

* * * * *